United States Patent [19]

Yim

[11] Patent Number: 4,684,716
[45] Date of Patent: Aug. 4, 1987

[54] POLYPEPTIDE INTERMEDIATES

[75] Inventor: Nelson C. Yim, Ambler, Pa.

[73] Assignee: SmithKline Beckman Corporation, Philadelphia, Pa.

[21] Appl. No.: 852,696

[22] Filed: Apr. 16, 1986

Related U.S. Application Data

[62] Division of Ser. No. 681,461, Dec. 14, 1984, Pat. No. 4,597,901.

[51] Int. Cl.$^4$ ................................................ C07K 7/16
[52] U.S. Cl. ........................................ 530/328; 530/329
[58] Field of Search ................................ 530/328, 329

[56] References Cited

U.S. PATENT DOCUMENTS

| 4,328,214 | 5/1982 | Rink et al. ............................ 424/177 |
| 4,367,225 | 1/1983 | Manning et al. ...................... 434/177 |
| 4,399,125 | 8/1983 | Manning et al. ...................... 424/177 |
| 4,469,679 | 9/1984 | Huffman et al. ...................... 530/328 |
| 4,481,193 | 11/1984 | Ali ........................................ 424/177 |
| 4,543,349 | 9/1985 | Callahan et al. ...................... 514/11 |
| 4,597,901 | 7/1986 | Yim ...................................... 530/328 |

OTHER PUBLICATIONS

M. Manning et al., Nature, 308 652 (1984).
M. Lebl et al., Proceedings of the 17th European Peptide Symposium, 1982.
Textbook of Biochemistry, 4th Ed., The Macmillan Co. N.Y., 1966, pp. 1475-1476.
Chemical Abstracts, vol. 83, 67 (1975) (Abstract No. 172906e).
Chemical Abstracts, vol. 85, 67 (1976) (Abstract No. 57024v).
Schroder and Lubke, The Peptides, vol. II, Academic Press, N.Y. 1966, pp. 366-373.
W. Rittel et al., *Experientia*, 32(2), 246-248 (1976).
Morrison and Boyd, *Organic Chemistry*, Allyn and Bacon, p. 1135 (1975).

*Primary Examiner*—Johnnie R. Brown
*Assistant Examiner*—F. T. Moezie
*Attorney, Agent, or Firm*—Mark R. Daniel; Janice E. Williams; Alan D. Lourie

[57] ABSTRACT

2- or 3-β-Indolylalanyl and β-indolylglycyl vasopressins are prepared by standard peptide synthetic methods. These 2- or 3-TRP vasopressins have vasopressin antagonist activity.

3 Claims, No Drawings

POLYPEPTIDE INTERMEDIATES

This is a division of application Ser. No. 681,461 filed Dec. 14, 1984, now U.S. Pat. No. 4,597,901.

This invention is related to cyclic octapeptide and nonapeptide vasopressin antagonists whose structures have a β-indolylalanyl or β-indolylglycyl unit at either the 2 or 3 position. These compounds are vasopressin antagonists whose biological activity is manifested as a water diuresis.

BACKGROUND OF THE INVENTION

Manning, Sawyer and coworkers have published a series of publications describing various vasopressin structures having a Pmp unit at position 1. Representative of these are U.S. Pat. Nos. 4,367,225 or 4,399,125 as well as Nature, 308 652 (1984).

Tryptophan is, of course, known to be a unit in other peptides such as the somatostatins (U.S. Pat. No. 4,320,214). It was also inserted at position 2 of oxytocin to give a compound with reduced oxytocic effect, M. Lebl et al., Proceedings of the 7th European Peptide Symposium, 1982.

The VSP antagonist compounds of the present invention have, at either the 2 or 3 position of their structures, a β-indolylalanyl or a β-indolylglycine. No VSP peptides to the best of my knowledge have been reported previously which have structures having a unit derived from an aromatic, bicyclic heterocyclic containing amino acid.

Certain of the peptide art designations used in the specification and claims are the following: Cap, β-mercapto-β,β-cycloalkylenepropionic acid; Pmp, β-mercapto-β,β-cyclopentamethylenepropionic acid; Chg, cyclohexylglycine; Abu, α-amino-n-butyric acid; Cha, cyclohexylalanine; Tyr, tyrosine; Tyr(Alk), O-alkyltyrosine; Phe, phenylalanine; Phe(4'-Alk), lower alkylphenylalanine; Val, valine; Nva, norvaline; Ile, isoluecine; Nle, norleucine; Leu, leucine; Ala, alanine; Lys, lysine; Arg, arginine; Harg, homoarginine; Asn, asparagine; Tos, tosylate; HF, hydrogen fluoride; BHA, benzhydrylamine; DIEA, diisopropylethylamine; 4-MeBzl, 4-methylbenzyl; TFA, trifluoroacetic acid; DCC, dicyclohexylcarbodiimide; HBT, 1-hydroxybenzotriazole; ADH, antidiuretic hormone; ACM, acetamidomethyl; DMAP, dimethylaminopyridine.

When the terms "vasopressin" or "VSP" are used, in the specification only, they mean L-arginine vasopressin (AVP) unless otherwise modified. The AVP derivatives of this invention are preferred. "Alk" represents a lower alkyl of 1-4 carbons which is optionally attached to the amide nitrogen at Y, to the oxygen substituent of the tyrosine unit when such is present at position 2 or to the phenyl ring of a phenylalanine unit such as at ring positions 2 or 3. Such alkyl substituents include methyl, ethyl, n-propyl, isopropyl or butyl.

Therefore, in the description herein and in the claims, the nomenclature common in the art of peptide and vasopressin chemistry is used. In certain designations such as the sulfur ring members, the key structural feature may be added for clarity. When no configuration is noted, the amino acid unit is in the L, or naturally occurring, form.

DESCRIPTION OF THE INVENTION

The TRP compounds of this invention are illustrated by the following structural formula:

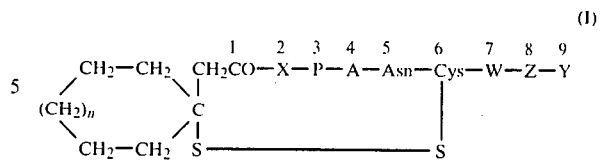

in which:

X is TRP or, when P is TRP, D-Phe, D-Phe(4'-Alk), D-Tyr, L-Tyr, D-Tyr(Alk) or L-Tyr(Alk);

P is Phe, Phe(4'-Alk) or, when X is other than TRP, TRP;

A is Val, Ile, Abu, Ala, Gly, Lys, Cha, Nle, Phe, Leu, Chg or Nva;

W is D-Pro or L-Pro;

Z is D-Arg, L-Arg, Harg, D-Lys or L-Lys;

Y is NH₂, NHAlk, OH, Gly, Gly(NH₂) or Gly(N-HAlk); and n is 0, 1 or 2; or a pharmaceutically acceptable salt, ester prodrug or complex thereof.

TRP is D-β-indolylalanyl (D-Trp), L-β-indolylalanyl (Trp), D-β-indolylglycyl (D-Ing), L-β-indolylglycyl (Ing), or N-formyl derivatives thereof. The latter are designated as either Trp(N-for) or Trp(N-CHO).

The novel TRP unit at either position 2 or 3 comprise the following compounds as chirally pure compounds or mixtures:

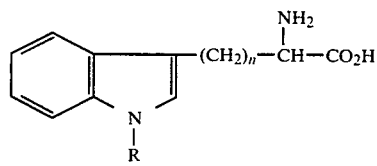

in which n is 0 or 1 and R is H or formyl.

Individual compounds of interest are [1-(β-mercapto-β,β-cyclopentamethylenepropionic acid)-2-D-tryptophan-4-valine-8-arginine]vasopressin, [1-(β-mercapto-β,β-cyclopentamethylenepropionic acid)-2-D-tryptophan(N-formyl)-4-valine-8-arginine]vasopressin and [1-(β-mercapto-β,β-cyclopentamethylenepropionic acid)-2-(O-ethyl-D-tyrosine)-3-L-β-indolylglycine-4-valine-8-arginine-9-desglycine]vasopressin.

Also included in this invention are various derivatives of the compounds of formula I such as addition salts, prodrugs in ester or amide form and complexes. The addition salts may be either salts with pharmaceutically acceptable cations such as NH₄⊕, Ca⊕⊕, K⊕ or Na⊕ at the terminal acid group (Y=OH) if present or with a pharmaceutically acceptable salt at a basic center of the peptide if present (as in the Arg unit). The acetate salt forms are especially useful and are often formed during the purification steps although hydrochloride, hydrobromide and salts with other strong acids are useful. The compounds, also, form inner salts or zwitter ions as when Y is OH. The ester prodrug forms are, for example, lower alkyl esters of the acids of formula I which have from 1-8 carbons in the alkyl radical or aralkyl esters such as various benzyl esters. Other latentiated derivatives of the compounds of formula I will be obvious to those skilled in the art. "Complexes" include various solvates, such as hydrates, or alcoholates or those with supporting resins, such as a Merrifield resin.

The compounds of formula I are prepared by cyclizing a linear octapeptide by means of the two mercapto groups, at the cysteine unit (Cys) at position 6 and at the β-mercapto-β,β-cycloalkylenepropionic acid unit (Cap) at position 1. The cyclization reaction occurs readily in the presence of a mild oxidizing agent capable of oxidizing a mercaptan to a disulfide. The reaction is represented as follows:

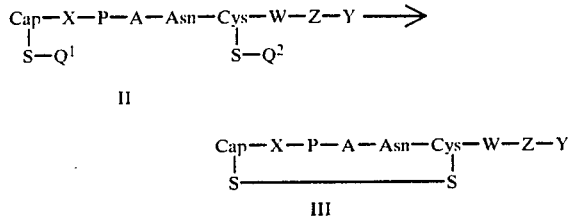

in which:

X, W, Y, Z, P and A are as defined for formula I with TRP preferably in the N-formyl form;

$Q^1$ and $Q^2$ are, each, hydrogen or a displaceable group. The preferred β-mercapto-β,β-cycloalkylenepropionic acid unit (Cap) is β-mercapto-β,β-cyclopentamethylenepropionic acid (Pmp).

The intermediates of formula II are new compounds and are a part of this invention.

The cyclization reaction of this reaction sequence is most usefully carried out by oxidation. Any oxidizing agent known to the art to be capable of converting a dimercaptan to a disulfide may be used. Exemplary of such agents are an alkali metal ferricyanide, especially potassium or sodium ferricyanide, oxygen or iodine.

As an example, potassium ferricyanide is added to the dimercaptan of formula II dissolved in a suitable inert solvent, for example, water or aqueous methanol at temperatures of from 0°-40°. Often, oxidation is at a pH of 7-7.5 at ambient temperature in dilute solution to give the cyclic compound.

The linear mercaptan starting material may or may not have displaceable protective groups common to the art ($Q^1$ and $Q^2$) present at the various amino acid units. Such protective groups include benzyl, p-methoxybenzyl, 1-adamantyl, t-butyl, p-nitrobenzyl, trityl, benzylthiomethyl, ethylcarbamoyl or acetamidomethyl. Benzyl, adamantyl or t-butyl are removed by mercuric (halo) acetate salts in aqueous methanol at 0°-80°. The protective group is usually removed before cyclization such as during the hydrogen fluoride splitting of the peptide from the supporting resin. It may, however, be removed either during the cyclization or, in situ, before cyclization.

The S-acetamidomethyl groups are especially useful. Iodine removes the S-protective group, especially the ACM group, and cyclizes the intermediate. Mercuric acetate or lead acetate also remove the ACM group to yield a metal mercaptide. This is converted to the thiol in situ by treatment with hydrogen sulfide. This, then, is oxidized in a separate step.

The desired cyclic octapeptide of formula I can be conveniently isolated by acidifying the aqueous oxidation mixture, such as using glacial acetic acid, and passing the reaction mixture over an ion-exchange chromatographic column, for example, over a weakly acid, acrylic resin column with acid elution, or by gel filtration over a bead-formed gel prepared by cross-linking dextran with epichlorohydrin.

As an alternative to the cyclization of the linear intermediates of formula II suggested above, the cyclized 6-Cys acids or 7-Pro acids (those of formula I in which either both tail units, W and Z, or only one tail unit, Z, are absent) are condensed with a protected dipeptide, W-Z-Y, or with an amino acid, Z-Y, respectively. The reaction of the Cys acid or the Pro acid with a suitably protected dipeptide or amino acid is carried out using any amide forming reaction common to the peptide art. Usually, substantially equimolar quantities of the starting materials are reacted in the presence of a carbodiimide, such as dicyclohexylcarbodiimide plus 1-hydroxybenzotriazole in an organic solvent at from b 0°-35°, preferably, from ice to room temperature. The protective groups are removed by a reaction which will not split the disulfide bond of the hexapeptide ring, for example, mild alkali.

The important intermediates of formula II are conveniently prepared using solid-phase methods of peptide synthesis as discussed in M. Manning, et al., J. Med. Chem. 25 46 (1982). A commercial benzhydrylamine support resin (BHA) is used to prepare the end products of formula I in which Y is $NH_2$ (the des-glycines) and a chloromethylbenzyl support resin (CMR) is used to prepare the compounds of formula I in which Y is OH (the des-glycinamides).

The peptide chain of the linear peptides of formula II is built up, stepwise, proceeding from unit 8 working toward unit 1. Each unit is properly protected as known in the peptide art and as described below. Alternatively, various oligopeptides may be built up using liquid or support reactions, then condensed as a last step in the reaction sequence for preparing the dimercapto intermediates.

The preferred sequence of resin support step reactions is conveniently carried out in a Beckman 990B peptide synthesizer without isolation of each intermediate peptide. The details of the procedure are in the working examples presented hereinafter. Solution or enzyme reaction conditions are applicable here as known to the art.

The various amino acids, which are consecutively added to the resin supported chain are protected as known to the art. For example, the Boc protecting group is used for an amino group especially at the α-position; N-formyl for indolyl; an optionally substituted benzyl, for the mercapto groups at the Pmp and Cys units; tosyl, for the Arg unit; and an optionally substituted carbobenzoxy (Z) for the Tyr or Lys units. The protective groups should, most conveniently, be those which are easily removed, that is, using acid treatment for the tert-butyloxycarbonyl group, sodium-liquid ammonia or catalytic hydrogenation for the benzyl or carbobenzoxy groups where the removal reaction conditions are not conducive to reaction at other portions of the peptide such as the disulfide bond.

As other examples of protecting groups, the amino group of an amino acid or oligopeptide is protected conventionally by an acyl group such as formyl, trifluoroacetyl, phthaloyl, p-toluenesulfonyl or o-nitrophenylsulfonyl group; a benzyloxycarbonyl group such as benzyloxycarbonyl, o-bromobenzyloxycarbonyl, p-bromobenzyloxycarbonyl, o- or p-chlorobenzyloxycarbonyl, p-nitrobenzyloxycarbonyl or p-methoxybenzyloxycarbonyl, an aliphatic oxycarbonyl group such as trichloroethyloxycarbonyl, t-amyloxycarbonyl, t-butoxycarbonyl or diisopropylmethoxycarbonyl, or an aralkyloxycarbonyl group such as 2-phenylisopropoxycarbonyl, 2-tolylisopropoxycarbonyl or 2-p- diphenylisopropoxycarbonyl. Amino groups are also protected by forming enamines by reaction with a 1,3-diketone such as benzoylacetone or acetylacetone.

The carboxyl groups can be protected by amide formation, hydrazide formation or esterification. The amide group is substituted, if necessary, with a 3,4-dimethoxybenzyl or bis-(p-methoxyphenyl)-methyl group. The hydrazide group is substituted with a benzyloxycarbonyl, trichloroethyloxycarbonyl, trifluoroacetyl, t-butoxycarbonyl, trityl or 2-p-diphenyl-isopropoxycarbonyl group. The ester group is substituted with an alkanol such as methanol, ethanol, t-butanol or cyanomethylalcohol; an aralkanol such as benzylalcohol, p-bromobenzylalcohol, p-nitrobenzylalcohol, 2,6-dichlorobenzylalcohol, benzhydrylalcohol, benzoylmethylalcohol, p-bromobenzoylmethylalcohol or p-chlorobenzoylmethylalcohol; a phenol such as 2,4,6-trichlorophenol, 2,4,5-trichlorophenol, pentachlorophenol, p-nitrophenol or 2,4-dinitrophenol; or a thiophenol such as thiophenol or p-nitrothiophenol. The hydroxy group in tyrosine is optionally protected by esterification or etherification. A group protected by esterification is, for example, an O-acetyl group; a O-benzoyl group, O-benzyloxycarbonyl or O-ethyloxycarbonyl. A group protected by etherification is, for example, an O-benzyl, O-tetrahydropyranyl or O-t-butyl group.

The amino group in the guanidino group in arginine can be protected by a salt forming, nitro, tosyl, benzyloxycarbonyl or mesitylene-2-sulfonyl group. However, it is not always necessary to protect the guanidino group.

The protected linear peptide intermediate is split from the carrying resin matrix, for example, by using ammonia in an alcoholic solvent when Merrifield resin is used, and, then, is treated to remove the protective groups, such as by using sodium-liquid ammonia. This procedure gives the preferred amide derivatives of the linear octapeptides.

More conveniently, the two steps are combined by treating the resin supported peptide with anhydrous hydrogen fluoride in the presence of a suitable cation scavenger as known to the art, such as anisole, to give the octapeptide intermediate of formula II, in dimercaptan form, and in good yield when BHA resin was used. In this case, when Merrifield resin is used, the acid (Y=OH) is obtained.

The compounds of this invention have potent vasopressin antagonist activity. Vasopressin is known to contribute to the anti-diuretic mechanism of action within the kidney. When the action of these compounds antagonizes that of the natural anti-diuretic hormone (ADH), the body excretes water due to an increased permeability of the terminal portions of the renal tubule. The mechanism of action is at the vasopressin receptors [$V_2$-receptors] located on the plasma membrane of certain renal epithelial cells. The most notable pharmocodynamic effect of the ADH antagonists of the invention is that of a water diuretic rather than of a natriuretic such as a thiazide.

Any patient suffering from the syndrome of inappropriate antidiuretic hormone secretion (SIADH) or from an undesirable edematous condition is a target for the claimed compounds. Examples of clinical conditions indicated for the compounds of this invention include hypertension, hepatic cirrhosis, congestive heart failure or a component of any traumatic condition resulting from serious injury or disease in which the agonism of naturally occurring vasopressin at the VSP-mediated receptor sites is a contributing factor.

The second group of vasopressin receptor sites are the vascular pressor sites ($V_1$-receptors) located within the cardiovascular system itself. Antagonism at the $V_2$ receptor sites results in vasodilation with an end result of anti-hypertensive activity. Treatment of dysmenorrhea is another utility for the compounds of this invention when administered intravenously or intranasally.

The compounds of this invention, therefore, are used to treat edema or to expel water in patients in need of such treatment by administering parenterally or by insufflation a nontoxic but effective quantity of the chosen compound, preferably combined with a pharmaceutical carrier. Dosage units of the active ingredient are selected from the range 5 mcg to 10 mg/kg, preferably 0.1 to 5 mg/kg, based on a 70 kg patient. The dosage units are applied from 1 to 5 times daily.

The pharmaceutical composition for inducing vasopressin antagonism contains an active ingredient of formula I in the form of a dosage unit as described above dissolved or suspended in a standard liquid carrier. A standard carrier is isotonic saline, contained in an ampoule or a multiple dose vial which is suitable for parenteral injection such as for intravenous, subcutaneous or intramuscular administration. A composition for insufflation is similar but is usually administered in a metered dose applicator or inhaler. Pulverized powder compositions may, also, be used, along with oily preparations, gels, buffers for isotonic preparations, emulsions or aerosols, as standard composition forms.

The compounds of this invention have been demonstrated to have unique antagonistic activity toward the natural antidiuretic hormone (anti-ADH activity), in vitro, in the medullary tissue of hog or human kidney and, in vivo, in the hydropenic rat or the hydropenic monkey. Details of the in vitro protocols are in F. L. Stassen et al., J. of Pharm. Exp. Ther. 233, 50–54 (1982) but the calculations of cyclase activity and binding potential at the receptor site are as follows:

Test Procedure for Assay of Adenylate Cyclase Activity

In each experiment the amount of $^{32}P$/cAMP formed in the absence of medullary membrane is determined (blank). The blank value is subtracted from all experimental data. The compound is tested for its effect on basal adenylate cyclase activity and/or on vasopressin stimulated activity. Each determination is carried out in triplicate. The Ka value is derived from a Lineweaver-Burke plot. Rel. $V_{max}=(V_{max}drug/V_{max}vasopressin)\times 100$. $K_i = I/[Ka'/Ka)-1]$ where I is the concentration of the antagonist, and Ka' and Ka are the concentrations of vasopressin required to give half-maximal activity of adenylate cyclase in the presence and absence of antagonist, respectively.

Test Procedure for Binding Assay

In each experiment, the amount of $^3H$-vasopressin bound in the absence and in the presence of an excess of vasopressin $(7.5\times 10^{-6}M)$ is measured in triplicate. These values represent total and non-specific binding, respectively. The $K_B$ of a compound is derived from the equation for competitive inhibition: $K_B=IC_{50}/(1+L/K_D)$, where $IC_{50}$ is the concentration required for 50% inhibition of specific $^3H$-vasopressin binding, L is the concentration of the ligand, and $K_D$ is the dissociation constant of $^3H$-vasopressin ($K_D=3.6\times 10^{-9}M$; 1 SD$=0.4\times 10^{-9}M$). This is the average $K_D$ value determined on 3 preparations of hog kidney membranes.

Hydropenic Rat Protocol

Food and water are removed from male rats approximately 18 hours prior to testing. Animals are housed 4 per metabolism cage. At 0 hour, the test compound is administered intraperitoneally to the test group and an equivalent volume of vehicle is administered to both control groups (fasted and non-fasted). Urine volume and osmolality are measured every hour for 4 hours. Test values are recorded as ml of urine excreted (cumulative), mEq/rat electrolyte excreted, mg/rat urea excreted, and osmolality in milli-Osmoles/kg $H_2O$. A tolerance test is used to determine significance. $ED_{300}$ is defined as the dose of compound (µg/kg) required to lower urine osmolality to 300 m-Osmoles/kg. $ED_{500}$ is defined as the dose of compound (µg/kg) required to lower urine osmolality to 500 m-Osmoles/kg. The hydropenic monkey protocol is similar.

TABLE I $$\begin{array}{c} CH_2\text{---}CH_2 \\ / \quad\quad\quad\backslash \\ CH_2 \quad\quad\quad CH_2CO\text{---}X\text{---}P\text{---}Val\text{---}Asn\text{---}Cys\text{---} \\ \backslash \quad\quad\quad / \\ CH_2\text{---}CH_2\text{---}S\text{---------------}S \\ \text{---}Pro\text{---}Arg\text{---}Gly(NH_2) \end{array}$$

| | | In Vitro (Pig) | | In Vivo (Rat) | |
|---|---|---|---|---|---|
| X | P | $K_I(M)$ | $K_B(M)$ | $ED_{300}$ (µg/kg) | $ED_{500}$ (µg/kg) |
| 1. D-Trp | Phe | $6.3 \times 10^{-8}$ | $1.3 \times 10^{-7}$ | 15.8 | — |
| 2. L-Trp | Phe | — | $2.1 \times 10^{-6}$ | >5,000 | 1,553 |
| 3. D-Trp(For) | Phe | — | $7.8 \times 10^{-8}$ | — | 13 |
| 4. L-Trp(For) | Phe | — | $8.4 \times 10^{-7}$ | >1,668 | 1,668 |

The following examples are intended solely to teach the preparation of the compounds of this invention. All temperatures are in degrees Centigrade.

EXAMPLE 1

Preparation of Boc-Phe-Val-Asn-Cys(S-Bzl)-Pro-Arg(Tos)-Gly-OCH$_2\phi$-Resin

Six millimoles (6 mmoles) of Boc-Phe-Val-Asn-Cys(S-Bzl)-Pro-Arg(Tos)-Gly-OCH$_2\phi$ Resin was prepared using 6 mmols of Boc-Gly-Merrifield resin, which is commercially available, as starting amino acid resin. The appropriately protected amino acids as noted were coupled sequentially onto the Boc-Gly resin by means of a Beckman Peptide Synthesizer Model #990B. In each coupling, 25 mmoles of Boc-amino acid and 0.5M (50 ml) of dicyclohexylcarbodiimide (DCC) coupling reagent was used. In the case of the coupling Asn moiety, 1-hydroxybenzotriazole (HBT, 25–50 mmoles) was also added and dry dimethylformamide was used as the solvent instead of methylene chloride.

Synthesis of

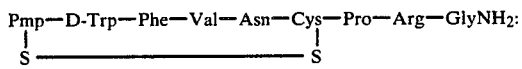
Pmp—D-Trp—Phe—Val—Asn—Cys—Pro—Arg—GlyNH$_2$:
  |                         |
  S————————————————————————S 1.5 Mmoles (4 grams) of protected peptide resin, Boc-Phe-Val-Asn-Cys(S-Bzl)-Pro-Arg(Tos)-Gly-OCH$_2\phi$-Resin was further sequentially coupled, first with 10 mmoles of Boc-D-Trp-OH with 20 ml of 0.5M DCC, and then with 10 mmoles of Pmp(S-Bzl) with 20 ml of 0.5M DCC and 1.2 gm of dimethylaminopyridine (DMAP).

The resulting protected peptide resin was washed with methylene chloride/ethanol and then methylene chloride and was finally dried in vacuo overnight. The dried peptide resin was subjected to ammonolysis using saturated ammonia/methanol (250 ml) at room temperature for three days. After evaporated to dryness under reduced pressure the residue was thoroughly extracted with dried dimethylformamide (50 ml total). The dimethylformamide extracts were combined and concentrated to 10 ml. Then a solid was precipitated with ether. The precipitated peptide was collected by filtration, and washed with ether, then dried in vacuo.

This crude protected peptide was dissolved in liquid ammonia (60 ml) and treated with sodium/liquid ammonia solution for deprotection of all the side chains to give Pmp(S-Na)-D-Trp-Phe-Val-Asn-Cys(SNa)-Pro-Arg-GlyNH$_2$ which was, then, oxidized in 4 liter of aqueous solution at pH 7–7.4 using 0.01M aqueous potassium ferricyanide solution. After complete oxidation, the pH of the aqueous solution was adjusted to pH 4.5 by addition of glacial acetic acid. This solution was passed through a weakly acidic ion exchange (Bio-Rex 70) column (11×2.5 cm) slowly. The column was, then, eluted with water and with aqueous pyridine/acetic acid buffer solution (4% acetic acid and 30% pyridine in water). The crude cyclized product was obtained in the pyridine/acetic acid buffer fractions. The solvent is concentrated and lyophilized from 0.2N aqueous acetic acid solution to give 582.5 mg crude of that product.

DETAILED PURIFICATION

1. Counter-Current Distribution:
   Sample: 450 mg crude, n-butanol/acetic acid/water (4:1:5)
   200 transfers
   Fractions 157–165 = 123 mg
2. Reverse-phase liquid chromatography (RPLC):
   25µ C-18 (40 grams) was packed in a glass column (15 cm×2.5 cm) by methanol, then, equilibrated with 50% acetonitrile in water followed by 0.1% trifluoroacetic acid for 2 hours.

| Sample: | | 123 mg Buffer A = 0.1% trifluoroacetic acid Buffer B = 0.25% trifluoroacetic acid/acetonitrile (4:6) A:B 150 ml:150 ml collecting 5 ml/fraction/6 min. |
|---|---|---|
| Fraction | 63–71 | 54.6 mg HPLC 95% pure |
|  | 72–81 | 42.3 mg HPLC 95% pure |
|  |  | 96.9 mg of product |

The combined product was further purified by 2nd RPLC:

| Fraction | 34–39 | 58 mg purest |
|---|---|---|
|  | 40–50 | 7 mg purest |
|  |  | 65 mg of total product obtained. |

3. Analysis:
   HPLC=96.2%
   TLC=1 spot
   Peptide content=84%

| Amino Acid Analysis: | | | | |
| --- | --- | --- | --- | --- |
| | Theory | Found | Theory | Found |
| NH$_3$ | 2 | 2.00 | Pro 1 | 1.36* |
| Arg | 1 | 1.03 | Gly 1 | 0.98 |
| Trp | 1 | 0.86 | CySH 1 | — |
| Asp | 1 | 0.99 | Val 1 | 0.92 |
| | | | Phe 1 | 0.91 |

EXAMPLE 2

Preparation of Boc-Phe-Val-Asn-Cys(S-4CH$_3$Bzl)-Pro-Arg(Tos)-Gly-BHA Resin

Three millimoles (3 mmoles) of Boc-Phe-Val-Asn-Cys(S-4-CH$_3$Bzl)-Pro-Arg(Tos)-Gly-BHA resin was prepared using 6 grams (3 mmoles) of commercially available p-methylbenzhydrylamine resin (MeBHA Resin) as starting material. The appropriately protected amino acids, including the Gly moiety, were coupled sequentially onto the MeBHA resin by means of Beckman Peptide Synthesizer Model #990B. In each coupling, 10 mmoles of the Boc amino acid and 20 ml of 0.5M DCC solution were used. In the case of the coupling Asn moiety, 1-hydroxybenzotrizole (HBT, 10–20 mmoles) was also added and dry dimethylformamide was used as solvent instead of methylene chloride.

Synthesis of Pmp—D-Trp(N—for)—Phe—Val—Asn—Cys—
  |                                                   |
  S———————————————————————————————————S —Pro—Arg—GlyNH$_2$:

One millimole (4 gm) of protected peptide resin, Boc-Phe-Val-Asn-Cys(S-4CH$_3$Bzl)-Pro-Arg(Tos)-Gly-BHA Resin from Example 2, was further sequentially coupled with 4 mmoles of Boc-N-formyl-D-tryptophan [Boc-D-Trp(N-for)-OH] and 4 mmoles of Pmp(S-4CH$_3$Bzl) with 4 mmoles of dimethylaminopyridine (DMAP) with DCC as coupling reagent in both cases. The final protected peptide resin, Pmp-(4CH$_3$Bzl)-D-Trp(N-for)-Phe-Val-Asn-Cys(S-CH$_3$Bzl)-Pro-Arg(Tos)-GlyBHA resin was washed with methylene chloride and, then, dried in vacuo overnight. It weighed 4.6 gm. In 5 ml of anisole, it was reacted with 50 ml of anhydrous hydrogen fluoride at 0° for one hour. After evaporation in vacuo at 0° to dryness, the resin was washed with anhydrous ether and was, then, extracted with diluted acetic acid. The combined extract was diluted to 4 liter with water immediately. The pH was adjusted to 7–7.4. Then, the mixture was oxidized with 0.01M of potassium ferricyanide solution until a pale yellowish color persisted.

Purification

587 Mg of crude product was isolated by passing over a Bio-Rex-70 ion exchange column and eluted by pyridine/acetic acid buffer as described above. 140 Mg of the crude product was purified by partition chromatography twice, RPLC twice and preparative HPLC to give 25 mg of pure titled product.

Analysis
  HPLC=95.3%
  TLC=1 spot
  Peptide content=66%

| Amino Acid Analysis: | | | | |
| --- | --- | --- | --- | --- |
| | Theory | Found | Theory | Found |
| NH$_3$ | 2 | 1.93 | Gly 1 | 1.01 |
| Arg | 1 | 1.02 | CysH 1 | 0.05 |
| Trp | 1 | 0.86 | Val 1 | 0.93 |
| Asp | 1 | 1.11 | Phe 1 | 0.95 |
| Pro | 1 | 1.37* | | |

EXAMPLE 3

Synthesis of Pmp—Trp(N—for)—Phe—Val—Asn—Cys—Pro—Arg—GlyNH$_2$:
  |                                                            |
  S————————————————————————————————————————S The procedure used is described above for the corresponding D-Trp(N-for)$^2$AVP analog. One millimole of protected peptide resin, Boc-Phe-Val-Asn-Cys(S-4CH$_3$Bzl)-Pro-Arg(Tos)-Arg-BHA resin, was further sequentially coupled with Boc-Trp(N-for)-OH and PMP(S-4CH$_3$Bzl) to give the protected Pmp(S-4CH$_3$Bzl)-Tyr(N-for)-Phe-Val-Asn-Cys(S-4CH$_3$Bzl)-Pro-Arg(Tos)-GlyBHA resin.

This protected nonapeptide was deprotected and cleaved from the resin by treatment with anhydrous hydrogen fluoride with anisole as scavanger. This deprotected peptide was extracted with diluted acetic acid and oxidized with 0.01M aqueous potassium ferricyanide solution in 4 liter of water at pH 7–7.4. A semipure product (93 mg) was obtained from a Bio-Rex 70 ion exchange column.

Purification

This 93 mg crude product was purified by RPLC with 0.1% trifluoroacetic acid and 0.25% trifluoroacetic acid/acetonitrile (40:60).

| Fraction | | |
| --- | --- | --- |
| | #36–37 | 22 mg (less pure) |
| | #38–42 | 34 mg (pure) |
| | #43–48 | 3.5 mg |

Analysis:
  HPLC=96%
  TLC=1 spot
  Peptide content=84%

| Amino Acid Analysis: | | | | |
| --- | --- | --- | --- | --- |
| | Theory | Found | Theory | Found |
| NH$_3$ | 2 | 1.89 | Gly 1 | 0.99 |
| Arg | 1 | 1.02 | CysH 1 | trace |
| Trp | 1 | 0.84 | Val 1 | 0.95 |
| Asp | 1 | 0.99 | Phe 1 | 0.96 |
| Pro | 1 | 1.40* | | |

*Proline value high due to incorporation of degradation products of cysteine.

EXAMPLE 4

Synthesis of

-continued

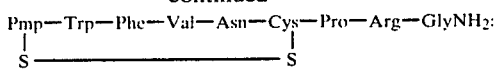

1.5 Mmoles (4 grams) of the protected peptide resin, Boc-Phe-Val-Asn-Cys(S-Bzl)-Pro-Arg(Tos)-Gly-OCH$_2\phi$-resin from Example 1 was further sequentially coupled with 10 mmole of Boc-L-Trp-OH with 20 ml of 0.5M DCC and 10 mmoles of Pmp(S-Bzl) with 20 ml of 0.5M DCC and 1.3 gm DMAP.

After ammonolysis, 2.2 grams of protected nonapeptide, Pmp(S-Bzl)-Trp-Phe-Val-Asn-Cys(S-Bzl)-Pro-Arg-(Tos)-GlyNH$_2$, was obtained.

1.5 Grams of this peptide was treated with sodium/liquid ammonia and, then, oxidized with 0.01M of aqueous ferricyanide solution. After passing over a Bio-Rex 70 ion exchange column, 303 mg crude cyclized produce was obtained as titled above.

Purification

285 Mg of the impure peptide was purified by CCD and 180 mg was obtained on transfers #192–218. The product was further purified by CM-52 ion exchange column, eluted with linear gradient aqueous ammonium acetate (0.01–0.1M) solution.

| Fraction | #41–61 | 41 mg |
| --- | --- | --- |
| | #62–83 | 49.5 mg |
| | #84–105 | 37 mg |

The 37 mg sample was further purified by G-25 Sephadex partition chromatograph column using 4:1:5/nBuOH:HOAc:H$_2$O system. Pure titled product (26 mg) was obtained in fractions 42–45.

The other two samples were combined and further purified by RPLC to yield another 28.2 mg pure product.

Analysis:
 HPLC=99%
 TLC=1 spot
 Peptide content=82%

| Amino Acid Analysis: | | | | |
| --- | --- | --- | --- | --- |
| | Theory | Found | Theory | Found |
| NH$_3$ | 2 | 1.64 | Gly 1 | 1.01 |
| Arg | 1 | 0.97 | CysH 1 | Trace |
| Trp | 1 | 0.97 | Val 1 | 0.87 |
| Asp | 1 | 1.01 | Phe 1 | 0.87 |
| Pro | 1 | 1.16* | | |

*High value due to incorporation of degradation products of cysteine.

EXAMPLE 5

Synthesis of Pmp—D-Trp—Phe—Val—Asn—Cys—Pro—Arg:

Pmp(S-Bzl)-S-D-Typ-Phe-Val-Asn-Cys(S-Bzl)-Pro-Arg(Tos)-Merrifield Resin (1.5 mmol), prepared as in Example 1, in 4.5 ml distilled anisole, is reacted with anhydrous hydrogen fluoride (40 ml) at 0° for one hour. After treatment as described above and evaporation in vacuo to dryness, the residue is treated with anhydrous ether and extracted with acetic acid from which one obtains the crude peptide. The completion of removal of the Bzl group from the Pmp moiety is carried out using the sodium in liquid ammonia reaction described above. The resulting unprotected octapeptide is cyclized using 0.01M potassium ferricyanide solution at pH 7–7.5 until color persists for 30 minutes again as described above in the preparation of the amide.

Desglycinamide octapeptide is collected after acidifying the oxidation solution with acetic acid to pH 4.5 and passing the reaction mixture over a Bio-Rex 70 column with acetic acid/pyridine buffer as eluent to give the titled compound.

EXAMPLE 6

Synthesis of Pmp—D-Ing—Phe—Val—Asn—Cys—Pro—ArgNH$_2$:

Pmp-(S4-MeBzl)-D-Ing-Phe-Val-Asn-Cys(S4-MeBzl)-Pro-Arg(Tos)-BHA resin, in 2 ml of anisole, is reacted with anhydrous hydrogen fluoride, 20 ml, at 0° for 50 minutes. The work up is done as usual and the uptake of ferricyanide is noted to give crude titled peptide.

EXAMPLE 7

Preparation of Pmp(S4-MeBzl)-D-Trp-Phe(4'-Et)-Val-Asn-Cys-(S4-MeBzl)-Pro-Arg(Tos)-BHA resin The titled resin-supported peptide is prepared from BOC-Arg(Tos) BHA resin (0.4 mmol/g) on a shaker using a protocol used before i.e. deprotection-coupling using HBT and DCC for 2 hours, up to Boc-Val-Asn-Cys(S4-MeBzl)-Pro-Arg(Tos)-BHA resin. The next two amino acid residues are coupled using the Beckman peptide synthesizer 990-B. The Pmp(S4-MeBzl) is coupled manually using DMAP-DCC overnight. The resin-containing peptide is washed and dried as usual to give the titled intermediate resin.

Synthesis of

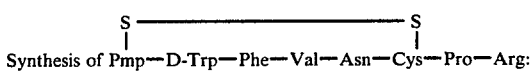

Pmp-(S4-MeBzl)-D-Trp-Phe(4-Et)-Val-Asn-Cys-(S4-MeBzl)-Pro-Arg(Tos)-BHA resin, in 3 ml of anisole is reacted with 30 ml of anhydrous hydrogen fluoride at 0° for an hour. The work up is done as described above, with 38 ml of ferricyanide. The desired crude peptide is obtained from the Bio-Rex column.

EXAMPLE 8

A. Synthesis of D,L-Indolylglycine (D,L-Ing)

D,L-Indolylglycine was prepared following the procedure disclosed in U.S. Pat. No. 3,920,730:
 61% yield m.p. 143.5° C.
 Anal. Calcd. for C$_{15}$H$_{18}$N$_2$O$_4$: C, 62.06; H, 6.25; N, 9.65; Found: C, 62.08; H, 6.38; N, 9.37.

B. Synthesis of Pmp(S-Bzl)-D-Tyr(Et)-D,L-Ing-Val-Asn-Cys(S-Bzl)-Pro-Arg(Tos)-Gly-NH$_2$ 1.5 Grams (1 mmole) of precursor peptide resin Boc-Val-Asn-Cys(S-Bzl)-Pro-Arg(Tos)-Gly-OCH$_2\phi$-resin was used: The peptide resin was prepared as noted above using Boc-Gly-Merrifield resin as starting material by coupling sequentially with the appropriate Boc-protected amino acids in a Beckman Peptide Synthesizer Model #990B.

After swelling in methylene chloride for 2 hours, the resin-supported peptide was further sequentially coupled with 3 mmoles of appropriate Boc amino acid and β(S-Bzl)-Pmp-OH by means of a Beckman Peptide Synthesizer 1.82 g of protected peptide resin Pmp(S-Bzl)-D-Tyr(Et)-Ing-Val-Asn-Cys(S-Bzl)-Pro-Arg(Tos)-Gly-OCH₂φ-resin was obtained after dried in vacuo.

This protected peptide resin was subjected to ammonialysis using saturated ammonia/methanol (300 ml) at room temperature for 3 days. After evaporated the reaction mixture to dryness under reduced pressure, the residue was thoroughly extracted with dried dimethylformamide (50 ml total). The combined dimethylformamide extract was concentrated to 10 ml and was then precipitated with ether. The precipitated titled peptide was collected by filtration and washed with ether, dried in vacuo: 0.965 grams.

C. Synthesis of

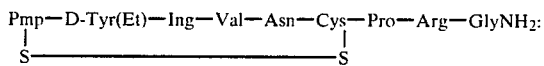

0.965 Grams of the protected peptide was dissolved in liquid ammonia (60 ml) and treted with sodium/liquid ammonia solution for deprotection of all the side chains. Subsequent oxidation with 0.01M of potassium ferricyanide solution in 4 liter of aqueous solution at pH 7.2 gave the desired product. 87 Ml of the aqueous ferricyanide was used. After complete oxidation, the pH was readjusted to 4.5. This solution was passed through a weakly acidic ion exchange (Bio-Rex 70) column slowly. The column was, then, eluted with a pyridine/acetic acid buffer solution (4% acetic acid, 30% pyridine in water). The eluent was concentrated and lyophilized from 0.2M acetic acid/water solution to give 530 mg crude titled product.

Purification of this crude product by counter current distribution gave 135 mg purified D,L mixture of desired product. FAB-MS gave (M+H) 1161 and (M−H) 1159 which corresponds to the desired molecular weight of the product of 1160. HPLC showed two major peaks. 63 Mg of this D,L mixture was subjected to preparative HPLC and 18.3 mg of one isomer and 10 mg of the other isomer were obtained using isocratic 70% water, 30% acetonitrile in 0.1% trifluoroacetic acid.

Both samples gave identical amino acid analysis and with a peptide content of 64-66% HPLC and TLC (ethyl acetate/n-butanyl/acetic acid/water (1:1:1:1) over silica) showed both are homogeneous but with different retention times and Rf values respectively.

EXAMPLE 9

Synthesis of
Pmp(S-Bzl)-D,L-Ing-Phe-Val-Asn-Cys(S-Bzl)-Pro-Arg(Tos)-Gly-NH₂

1.5 Gram (1 mmole) of precursor peptide resin, Boc-Phe-Val-Asn-Cys(S-Bzl)-Pro-Arg(Tos)-Gly-OCH₂φ-resin, which was prepared using Boc-Gly-Merrifield resin as starting material by coupling sequentially with appropriate BOC-protected amino acids in a Beckman Peptide Synthesizer, was used. The precursor was further coupled with 3 mmoles of Boc-Ing-OH and β-(S-Bzl)-Pmp-OH, sequentially, in a Beckman Peptide Synthesizer. 1.96 Grams of titled protected peptide attached to the resin was obtained after drying in vacuo.

This protected peptide resin was subjected to ammonialysis using saturated ammonia/methanol (300 ml) at room temperature for 3 days. After evaporating the mixture to dryness under reduced pressure, the residue was thoroughly extracted with dimethylformamide. The combined extract was concentrated to 10 ml and, then, was precipitated with ether. The precipitated titled peptide was collected by filtration, washed with ether and dried in vacuo: 1.12 g.

EXAMPLE 10

Synthesis of

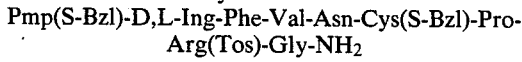

1.1 gram of the protected peptide from Example 9 was dissolved in liquid ammonia (60 ml) and treated with sodium/liquid ammonia solution. Subsequent oxidation with 0.01M of potassium ferricyanide solution gave the cyclized product. 89 Ml of the solution was utilized for the oxidation. After passing through a Bio-Rex 70 column and eluting with pyridine/acetic acid buffer, 269 mg of crude product was obtained.

This crude product was purified by counter current distribution and G-25 gel filtration methods. 52 Mg crude titled product was obtained which demonstrated two isomers in TLC and HPLC.

EXAMPLE 11

Other representative compounds are prepared by substituting appropriate protected amino acids in the synthetic routes described in detail above:

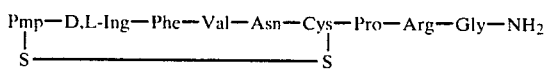

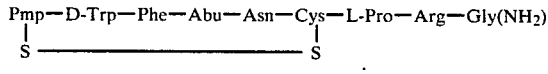

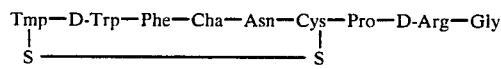

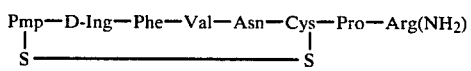

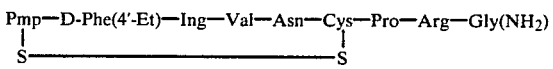

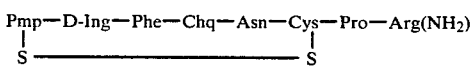

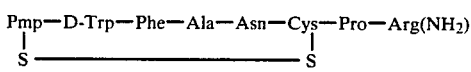

EXAMPLE 12

Parenteral Dosage Unit Compositions

A preparation which contains 500 mcg of the cyclic octapeptide of Examples 1 or 4 as a sterile dry powder for parenteral injection is prepared as follows: 0.5 mg of peptide amide is dissolved in 1 ml of an aqueous solution of 20 mg of mannitol. The solution is filtered under sterile conditions into a 2 ml ampoule and lyophilized.

The powder is reconstituted before either intramuscular or intravenous injection to a subject suffering from edema susceptible to anti-ADH mechanism of action. The injection is repeated as necessary, from 1-5 times daily or in continuous i.v. drug injection. Other octapeptides of this invention are made up and used in like manner.

Nasal Dosage Unit Compositions 30 mg of finely ground octapeptide of this invention such the product of Example 2 is suspended in a mixture of 75 mg of benzyl alcohol and 1.395 g of a suspending agent such as a commercial mixture of semisynthetic glycerides of higher fatty acids. The suspension is placed in an aerosol 10 ml container which is closed with a metering valve and charged with aerosol propellants. The contents comprise 100 unit doses which are administered intranasally to an edematous subject from 1-6 times a day.

What is claimed is:

1. A polypeptide compound of the formula:

$$\begin{array}{c} \text{Cap}-\text{X}-\text{P}-\text{A}-\text{Asn}-\text{Cys}-\text{W}-\text{Z}-\text{Y} \\ | \quad\quad\quad\quad\quad\quad\quad | \\ \text{S}-\text{Q}^1 \quad\quad\quad\quad \text{S}-\text{Q}^2 \end{array}$$

in which:
  Cap is $\beta$-mercapto-$\beta,\beta$-cycloalkylenepropionic acid;
  X is TRP or, when P is TRP, X is D-Phe, D-Phe(4'-Alk), D-Tyr, L-Tyr, D-Tyr(Alk) or L-Tyr(Alk);
  P is Phe, Phe(4'-Alk) or, when X is other than TRP, P is TRP;
  A is Val, Ile, Abu, Ala, Gly, Lys, Cha, Nle, Phe, Leu, Chg or Nva;
  W is D-Pro or L-Pro;
  Z is D-Arg, L-Arg, HArg, D-Lys or L-Lys
  $Q^1$ and $Q^2$ are each hydrogen;
  Y is $NH_2$, NHAlk, OH, Gly, Gly($NH_2$) or Gly(NHAlk); Alk is a lower alkyl of 1-4 carbons; and TRP is D-Trp, Trp, D-Ing, Ing, or N-formyl derivatives thereof.

2. The compound of claim 1 in which:
  Cap is Pmp;
  X is D-Trp or N-formyl derivatives thereof;
  P is Phe;
  A is Val;
  W is L-Pro;
  Z is L-Arg; and
  Y is $NH_2$ or Gly($NH_2$).

3. The compound according to claim 2 in which Pmp is $\beta$-mercapto-$\beta,\beta$-cyclopentamethylenepropionic acid.

* * * * *